United States Patent [19]

Wagle et al.

[11] Patent Number: 5,284,664
[45] Date of Patent: Feb. 8, 1994

[54] METHOD OF TREATING THE SYMPTOMS OF ALZHEIMER'S DISEASE

[75] Inventors: Sudhakar S. Wagle, Mequon, Wis.; Thomas Steinbach, Houston, Tex.; Carl H. Lawyer, Mequon, Wis.; William J. Hermann, Sealy, Tex.; Ali A. S. Gawish, Mequon, Wis.

[73] Assignee: Kremers-Urban Company, Mequon, Wis.

[21] Appl. No.: 835,029

[22] Filed: Feb. 5, 1992

Related U.S. Application Data

[63] Continuation-in-part of Ser. No. 803,844, Dec. 4, 1991, which is a continuation-in-part of Ser. No. 728,267, Jul. 11, 1991, abandoned, which is a continuation of Ser. No. 228,364, Aug. 4, 1988, Pat. No. 5,055,296.

[51] Int. Cl.$^5$ .......................................... A61K 35/407
[52] U.S. Cl. .......................................... 424/553
[58] Field of Search ........................................ 424/553

[56] References Cited

U.S. PATENT DOCUMENTS

| | | | |
|---|---|---|---|
| 3,778,510 | 12/1973 | Blonde | 424/553 |
| 4,148,788 | 4/1979 | Wang | 530/524 |
| 4,420,398 | 12/1983 | Castino | 210/641 |
| 4,426,324 | 1/1984 | Meienhofer | 530/307 |
| 4,428,938 | 1/1984 | Kisfaludy | 514/17 |
| 4,464,355 | 8/1984 | Fabricius | 424/85.2 |
| 4,468,379 | 8/1984 | Gottlieb | 424/534 |
| 4,537,878 | 8/1985 | Plotnikoff | 514/2 |
| 4,595,588 | 6/1986 | Baron | 424/89 |
| 4,595,780 | 6/1986 | Ogata | 564/79 |
| 4,596,798 | 6/1986 | Shipman, Jr. | 514/183 |
| 4,598,095 | 7/1986 | Nishimura | 514/632 |
| 4,602,037 | 7/1986 | Seborm | 514/512 |
| 4,603,122 | 7/1986 | Blough | 514/23 |
| 4,603,219 | 7/1986 | Verheyden | 560/255 |
| 4,604,404 | 8/1986 | Munson, Jr. | 514/494 |
| 4,605,658 | 8/1986 | Holy | 514/261 |
| 4,605,659 | 8/1986 | Verheyden | 514/262 |
| 4,606,917 | 8/1986 | Eppstein | 424/85.6 |
| 4,609,661 | 9/1986 | Verheyden | 514/262 |
| 4,609,662 | 9/1986 | Krenitsky | 514/262 |
| 4,612,314 | 9/1986 | Verheyden | 514/261 |
| 4,614,651 | 9/1986 | Jarvis, Jr. | 424/85.4 |
| 4,614,731 | 9/1986 | Horecker | 514/18 |
| 4,617,304 | 10/1986 | Ashton | 514/261 |
| 4,621,140 | 11/1986 | Verheyden | 544/276 |
| 4,622,430 | 11/1986 | Dekker | 564/458 |
| 4,625,026 | 11/1986 | Kim | 544/249 |
| 4,626,524 | 12/1986 | Server | 514/13 |
| 4,628,063 | 12/1986 | Haines | 514/626 |
| 4,629,811 | 12/1986 | Dominianni | 564/99 |
| 4,631,149 | 12/1986 | Rinehart, Jr. | 540/546 |
| 4,644,055 | 2/1987 | Kettner | 530/330 |
| 4,668,660 | 5/1987 | Paessens | 514/383 |
| 4,670,437 | 6/1987 | Abdulla | 514/247 |
| 4,699,898 | 10/1987 | Gottlieb | 514/18 |
| 4,708,818 | 11/1987 | Montagnier | 435/5 |
| 4,710,380 | 12/1987 | Gottlieb | 424/534 |

FOREIGN PATENT DOCUMENTS 0140134 5/1985 European Pat. Off.
0250234 12/1987 European Pat. Off.
357958 3/1990 European Pat. Off.

OTHER PUBLICATIONS

Andrews et al., *JAMA*, 146, 1107 (1951).
Barksdale, *South. Med. Jour.*, 50, 1524 (1957).
Barksdale, et al., *Virginia Medical Monthly*, 81, 321 (1954).
Barrock, *Medical Times*, 1, (Aug. 1958).
Boreen, *Minnesota Medicine*, 25, 276 (1942).
Burks, Jr., *Journal of the Louisiana Medical Society*, 106, 92 (1954).
Burks, Jr. and Knox. *Archives of Dermatology and Syphilology*, 70 508 (1954).
Center for Disease Control, Dept. Health and Human Services, *Chronic Fatigue Syndrome*, Mar. 22, 1988.
Chase, *Wall Street Journal*, Apr. 28, 1988, at 14, at col. 1.
Gaskell, *Brit. Med. J.*, 1037 (Jun. 11, 1949).
Gathings, *Am. J. Surgery*, 88, 429 (1954).
Harris, et al., *Oral Surgery*, 7, 239 (1954).
Hellinger, et al., *JAMA*, 260, 971 (Aug. 19, 1988).
Heywood, *Clinical Medicine*, 3, 425 (1956).
Hjerten, *Archives of Biochemistry and Biophysics*, Suppl. 1, 147 (1962).
Hjerten and Mosbach, *Analytical Biochemistry*, 3, 109 (1962).
Holtman, *Oral Surgery*, 7, 12 (1954).
Judge, *Proc. Soc. Exptl. Biol. Med.*, 123, 199 (1966).
Kozelka and Marshall, *Clinical Medicine*, 3, 245 (1956).
Kutapressin-Drug Package Insert, Kremers-Urban.
Li, et al., *Nature*, 219, 1163 (Sep. 14, 1968).
Li, et al., *Proc. Soc. Exptl. Biol. Med.*, 114, 504 (1963).
Li, et al., *Proc. Soc. Exptl. Biol. Med.*, 109, 534 (1962).
Li et al., *J. Nat'l Cancer Inst.*, 41, 1249 (Nov. 1968).
Li, et al., *Ann. N.Y. Acad. Sci.*, 130, 374 (1965).
Lichtenstein and Stillians, Arch. Dermatology and Syphilology, 45, 595 (1942).
Lubowe, *Clinical Medicine*, 59, 8 (1952).

(List continued on next page.)

Primary Examiner—Douglas W. Robinson
Assistant Examiner—Jean C. Witz
Attorney, Agent, or Firm—Tilton, Fallon, Lungmus & Chestnut

[57] ABSTRACT

A therapeutic method for treating Alzheimer's or related disease. The method comprises administering a therapeutically-effective amount of a mammalian liver extract, the extract being characterized by being heat stable, insoluble in acetone and soluble in water, peptide or peptide fragment selected from the groups consisting of Sequence Identification Numbers 1-9.

5 Claims, 5 Drawing Sheets

OTHER PUBLICATIONS

Marshall, et al., *Am. J. Surgery*, 90, 47 (1955).
Marshall, Maryland State Med. J., (Jun. 1960).
Marshall, *Am. J. Surgery*, 84(6), 675 (1952).
Marshall, and Schadeberg, *Wisconsin Medical Journal*, 49, 369 (1950).
Marshall and Schadeberg, *Indian J. Veneral Diseases*, 16, 89 (1950).
Marshall, J.M.A. Alabama, 13, 255 (1944).
Marshall, *Mississippi Valley Med. J.*, 61, 172 (1939).
Marshall, *Med. World*, 57, 101 (1939).
Marshall, *Northwest Medicine*, 38, 467 (1939).
Marshall, *J. Invest. Derm.*, 2, 105 (1939).
Marshall, *A. J. Surgery*, 448 (Oct. 1951).
Marshall, *Medical Times*, 70, 222 (1951).
Marshall, *Indian J. Veneral Diseases and Dermatology*, 20, 99 (1954).
Marshall, *the Journal-Lancet*, 60, 117 (1940).
Marshall, *Minnesota Medicine*, 25, 796 (1942).
Marshall, *Arizona Medicine*, 14(1), 11 (1957).
Marshall, *Mississippi Valley Med. J.*, 76, 199 (1954).
Mitchell-Heggs, *Brit. Med. J.*, 2, 1079 (1951).
Montefiori, et al., *J. Clin. Micro.*, 26, 231 (Feb. 1988).
Montefiori and Mitchell, *Proc. Nat'l. Acad. Sci. U.S.A.*, 84(9), 2985 (May 1987).
National Formulary, vol. XII, p. 222.
National Formulary, vol. XI, pp. 192-194.
Nierman, *Journal of the Indiana State Medical Association*, 45, 497 (1952).
Osbahr, et al., *Biochim. Biophys. Acta.*, 86, 535 (1964).
Pensky and Goldberg, *The Journal-Lancet*, 75(11), 490 (Nov. 1955).
Pensky and Goldberg, *New York State Journal of Medicine*, 53, 2238 (1953).
*Pharmacopeia of the United States*, 15, 379.
Pollner, *Medical World News*, 35 (Jun. 13, 1988).
Poole, *South. Med. J.*, 50, 207 (1957).
Ruggieri, *Science*, 194, 491 (1976).
Schmeer and Huala, *Ann. N.Y. Acad. Sci.*, 118, 605 (1965).
Schmeer, *Science*, 144, 413 (1964).
Smith, *HIV and Other Highly Pathogenic Viruses*, Academic Press, Inc. (1988).
Stillians, *Mississippi Valley Medical Journal*, 64, 135 (1942).
Stokes and Sternberg, *Archives of Dermatology and Syphilology*, 40, 345 (1939).
Sutton, *Archives of Dermatology and Syphilology*, 18, 887 (1928).
Tweksbury and Stahmann, *Arch. Biochem. Biophys. (U.S.)*, 112, 453 (1965).
Tewksbury, *Archives Int'l de Pharmacodynamic et de Therapie*, 173, 426 (1968).
Tewksbury, *Dissertation Absttracts International-Part II*, 25-04, 2214 (1964).
Walters, *Ohio State Medical Journal*, 44, 697 (1948).
White, *The letters of the International Correspondence Society of Allergists*, 19, 30 (1956).

KU214 and 215 peptide:

5'GGGCCGCATGGGCAAAGTATTATGCTCGGCCTGAACAGTGTATTTATCCAAGTGCAATATACGTCAAGCTGCACCTTTT
3'CCCGGCGTACCCGTTTCATAATACGAGCCGGACTTGTCACATAAATAGGTTCACGTTATTATGCAGTTCGACGTGGAAAA

TTTGACTTCTGCTGG    CTATAAATGTGCATTTATCAGAAGTTGATGTAACACTATTCTAGTACTGTTCCTTCATCTAGA
AAACTGAAGACGACC...GATATTTACACGTAAATAGTCTTCAACTACATTTGTGATAAGATCATGACAAGGAAGTAGATCT

TTGATCAATTTTAATTAAAATTAAGCACTAAAAAAAAAAA    CTATCGATTCTGGAACCTTCAGAGGJ
AACTAGTTAAAATTAATTTTAATTCGTGATTTTTTTTTTT...GATAGCTAAGACCTTGGAAGTCTCC5'

5'CATGGICCICATGGI3' PRIMER-1

5'CCTCTGAAGGTTCCAGAATCGATAG3' PRIMER-2    (CLONTECH UNI-AMP PRIMER)

| denature, re-anneal
Cycle 1    |
           v 5'GGGCCGCATGGGCAAAGTATTATGCTCGGCCTGAACAGTGTATTTATCCAAGTGCAATATACGTCAAGCTGCACCTTT
TTTTGACTTCTGCTGG...CTATAAATGTGCATTTATCAGAAGTTATGTAAACACTATTCTAGTACTGTTCCTTCATCTAG
ATTGATCAATTTTAATTAAAATTAAGCACTAAAAAAAAAA...CTATCGATTCTGGAACCTTCAGAGG3'
                                                    :::::::::::::::::
                                              3'GATAGCTAAGACCTTGGAAGTCTCC5'

PRIMER-2 EXTENDS <--------------- EXTENDS

5'CATGGICCICATGGI3' PRIMER-1
:::::::::::::::
3'    CCCGGCGTACCCGTTTCATAATACGAGCCGGACTTGTCACATAAATAGGTTCACGTTATTATGCAGTTCGACGTGG
AAAAACTGAAGACGACCGATATTTACACGTAAATAGTCTTCAACTACACTTGTGATAAGATCATGACAAGAAGTAGATC
TAACTAGTTAAAATTAATTTTAATTCGTGATTTTTTTTTTTTTTTGATAGCTAAGACCTTGGAAGTCTCC5'

| Polymerase, dNTPs
Cycle 1    |
           v

Fig. 2A (cont.)

```
5'GGGCCGCATGGGCCAAAGTATTATGCTCGGCCTGAACAGTGTATTTATCCAAGTGCAATAATACGTCAAGCTGCACCTTTT
3'CCCGGCGTACCCGTTTCATAATACGAGCCGGACTTGTCACATAAATAGGTTCACGTTATGCAGTTCGACGTGGAAAA
 TTTGACTTCTGCTGG    CTATAAATGTGCATTTATCAGAAGTTGATGTAAACACTATTCTAGTACTGTTCCTTCATCTAGA
 AACTGAAGACGACC...GATATTTACACGTAAATAGTCTTCAACTACATTGTGATAAGATCATGACAAGGAAGTAGATCT
 TTGATCAATTTTAATTAAGCACTAAAAAAAAAA            CTATCGATTCTGGAACCTTCAGAGG3'
 AACTAGTTAAATTAATTTAATTCGTGATTTTTTTTTTT...GATAGCTAAGACCTTGGAAGTCTCC5'

5'GGGCCGCATGGGCCAAAGTATTATGCTCGGCCTGAACAGTGTATTTATCCAAGTGCAATAATACGTCAAGCTGCACCTTTT
3'CCCGGCGTACCCGTTTCATAATACGAGCCGGACTTGTCACATAAATAGGTTCACGTTATGCAGTTCGACGTGGAAAA
 TTTGACTTCTGCTGG    CTATAAATGTGCATTTATCAGAAGTTGATGTAAACACTATTCTAGTACTGTTCCTTCATCTAGA
 AACTGAAGACGACC...GATATTACACGTAAATAGTCTTCAACTACATTGTGATAAGATCATGACAAGGAAGTAGATCT
 TTGATCAATTTTAATTAAGCACTAAAAAAAAAA            CTATCGATTCTGGAACCTTCAGAGG3'
 AACTAGTTAAAATTAATTTAATTCGTGATTTTTTTTTTT...GATAGCTAAGACCTTGGAAGTCTCC5'

Cycle 2   | denature, re-anneal
                        v

5' GGGCCGCATGGGCCAAAGTATTATGCTCGGCCTGAACAGTGTATTTATCCAAGTGCAATAATACGTCAAGCTGCACCTTT
   TTTGACTTCTGCTGG...CTATAAATGTGCATTTATCAGAAGTTGATGTAAACACTATTCTAGTACTGTTCCTTCATCTAG
   ATTGATCAATTTAATTAAGCACTAAAAAAAAAAAA...CTATCGATTCTGAACCTTGGAAGTCTCAGAGG3'

PRIMER-2 EXTENDS <--------  3' GATAGCTAAGACCTTGGAAGTCTCC 5'

5' CATGGTCCCTCATGGG 3' PRIMER-1 --------> EXTENDS
   ::::::::::::::
3' CCCGGCGTACCCGTTTCATAATACGAGCCGGACTTGTCACATAAATAGGTTCACGTTATTATGCAGTTCGACGTGG
   AAAAACTGAAGACGACCGATATTACACGTAAATAGTCTTCAACTACATTTGTGATAAGATCATGACAAGGAAGTAGATC
   TAACTAGTTAAAATTAATTTTTTGATAGCTAAGACCTTGGAAGTCTCC5'
5' GGGCCGCATGGGCCAAAGTATTATGCTCGGCCTGAACAGTGTATTTATCCAAGTGCAATAATACGTCAAGCTGCACCTTT
```

Fig. 2B

```
TTTTGACTTCTGCTGG...CTATAAATGTGCATTTATCAGAAGTTGATGTAAACACTATTCTAGTACTGTTCCTTCATCTAG
ATTGATCAATTTTAATTAAGCACTAAAAAAAAAA...CTATCGATTCTGGAACCTTCAGAGG3'
                                     :::::::::::::::::::::::::::
            PRIMER-2 EXTENDS <-------------3'GATAGCTAAGACCCTTGGAAGTCTCC5'

5'CATGGICCICATGGI3' PRIMER-1 ------------> EXTENDS
    ::::::::::::::::
3'___CCCGGGTACCCGTTTCATAATACGAGCCGACTTGTCACATAAAATAGGTTCACGTTATTATGCAGTTCGACGTGG
AAAAAACTGAAGACGACCGATATTTACACGTAAATAGTCTTCAACTACATTTGTGATAAGATCATGACAAGGAAGTAGATC
TAACTAGTTAAATTAATTCGTGATTTTTTTTTTTTGATAGCTAAGACCCTTGGAAGTCTCC5'

|
                Cycle 2  |  Polymerase, dNTPs
                         v

5'GGGCCGCATGGGCAAAGTATTATGCTCGGCCTGAACAGTGTATTTATCCAAGTGCAATAATACGTCAAGCTGCACCTTTT
3'CCCGGGTACCCGTTTCATAATACGAGCCGGACTTGTCACATAAATAGGTTCACGTTATTATGCAGTTCGACGTGGAAAA
TTTGACTTCTGCTGG  CTATAAATGTGCATTTATCAGAAGTTGATGTAAACACTATTCTAGTACTGTTCCTTCATCTAGA
AACTGAAGACGACC...GATATTTACACGTAAATAGTCTTCAACTACATTTGTGATAAGATCATGACAAGGAAGTAGATCT
TTGATCAATTTTAATTAAAATTAAGCACTAAAAAAAAAAA  CTATCGATTCTGGAACCTTCAGAGG3'
AACTAGTTAAAATTAATTTTAATTCGTGATTTTTTTTTTT...GATAGCTAAGACCTTGGAAGTCTCC5'
```

Fig. 2B (cont.)

```
5'GGGCCCGCATGGGCAAAGTATTATGCTCGGCCTGAACAGTGTATTTTATCCAAGTGCAATAATACGTCAAGCTGCACCTTTT
3'CCCGGGCGTACCCGTTTCATAATACGAGCCGGACTTGTCACATAAAATAGGTTCACGTTATTATGCAGTTCGACGTGGAAAA
TTTGACTTCTGCTGG    CTATAAATGTGCATTTATCAGAAGTTGATGTAAACACTATTCTAGTACTGTTCCTTCATCTAGA
AAACTGAAGACGACC···GATATTTACACGTAAATAGTCTTCAACTACATTTGTGATAAGATCATGACAAGGAAGTAGATCT
TTGATCAATTTTAATTAAAATTAAGCACTAAAAAAAAAAA      CTATCGATTCTGGAACCTTCAGAGG3'
AACTAGTTAAAATTAATTTAATTCGTGATTTTTTTTTTT···GATAGCTAAGACCTTGGAAGTCTCC5'

5'GGGCCCGCATGGGCAAAGTATTATGCTCGGCCTGAACAGTGTATTTTATCCAAGTGCAATAATACGTCAAGCTGCACCTTTT
3'CCCGGGCGTACCCGTTTCATAATACGAGCCGGACTTGTCACATAAAATAGGTTCACGTTATGCAGTTCGACGTGGAAAA
TTTGACTTCTGCTGG    CTATAAATGTGCATTTATCAGAAGTTGATGTAAACACTATTCTAGTACTGTTCCTTCATCTAGA
AAACTGAAGACGACC···GATATTTACACGTAAATAGTCTTCAACTACATTGTGATAAGATCATGACAAGGAAGTAGATCT
TTGATCAATTTTAATTAAAATTAAGCACTAAAAAAAAAAA      CTATCGATTCTGGAACCTTCAGAGG3'
AACTAGTTAAAATTAATTTAATTCGTGATTTTTTTTTTT···GATAGCTAAGACCTTGGAAGTCTCC5'

5'GGGCCCGCATGGGCAAAGTATTATGCTCGGCCTGAACAGTGTATTTTATCCAAGTGCAATAATACGTCAAGCTGCACCTTTT
3'CCCGGGCGTACCCGTTTCATAATACGAGCCGGACTTGTCACATAAAATAGGTTCACGTTATGCAGTTCGACGTGGAAAA
TTTGACTTCTGCTGG    CTATAAATGTGCATTTATCAGAAGTTGATGTAAACACTATTCTAGTACTGTTCCTTCATCTAGA
AAACTGAAGACGACC···GATATTTACACGTAAATAGTCTTCAACTACATTGTGATAAGATCATGACAAGGAAGTAGATCT
TTGATCAATTTTAATTAAAATTAAGCACTAAAAAAAAAAA      CTATCGATTCTGGAACCTTCAGAGG3'
AACTAGTTAAAATTAATTTAATTCGTGATTTTTTTTTTT···GATAGCTAAGACCTTGGAAGTCTCC5'
``` further Cycles
|
v

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( C ) STRANDEDNESS: unknown
        ( D ) TOPOLOGY: unknown     ( i i ) MOLECULE TYPE: peptide     ( x i ) SEQUENCE DESCRIPTION: SEQ ID NO:1:

```
Gly Pro His Gly Gln Ser Ile Met Leu Gly Leu Asn Ser Val Phe Tyr
 1               5                  10                  15

Pro Ser Ala Ile Ile Arg Gln Ala Ala Pro Phe Phe Asp Phe Cys Trp
                20                  25                  30
```

( 2 ) INFORMATION FOR SEQ ID NO:2:

( i ) SEQUENCE CHARACTERISTICS:
        ( A ) LENGTH: 96 base pairs
        ( B ) TYPE: nucleic acid
        ( C ) STRANDEDNESS: unknown
        ( D ) TOPOLOGY: unknown (i i) MOLECULE TYPE: DNA (genomic)

(x i) SEQUENCE DESCRIPTION: SEQ ID NO:2:

GGGCCGCATG GGCAAAGTAT TATGCTCGGC CTGAACAGTG TATTTTATCC AAGTGCAATA    60

ATACGTCAAG CTGCAGCTTT TTTTGACTTC TGCTGG    96

(2) INFORMATION FOR SEQ ID NO:3:

(i) SEQUENCE CHARACTERISTICS:
        (A) LENGTH: 110 base pairs
        (B) TYPE: nucleic acid
        (C) STRANDEDNESS: unknown
        (D) TOPOLOGY: unknown     (i i) MOLECULE TYPE: DNA (genomic)

(x i) SEQUENCE DESCRIPTION: SEQ ID NO:3:

CTATAAATGT GCATTTATCA GAAGTTGATG TAAACACTAT TCTAGTACTG TTCCTTCATC    60

TAGATTGATC AATTTTAATT AAAATTAAGC ACTAAAAAAA AAAAAAAAAA    110

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown     (i i) MOLECULE TYPE: peptide     (x i) SEQUENCE DESCRIPTION: SEQ ID NO:4:

Tyr Lys Cys Ala Phe Ile Arg Ser
1               5

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown     (i i) MOLECULE TYPE: DNA (genomic)

(x i) SEQUENCE DESCRIPTION: SEQ ID NO:5:

CTATAAATGT GCATTTATCA GAAGT    25

(2) INFORMATION FOR SEQ ID NO:6:

(i) SEQUENCE CHARACTERISTICS:
        (A) LENGTH: 21 amino acids
        (B) TYPE: amino acid
        (C) STRANDEDNESS: unknown
        (D) TOPOLOGY: unknown     (i i) MOLECULE TYPE: peptide     (x i) SEQUENCE DESCRIPTION: SEQ ID NO:6:

Ile Asn Val His Leu Ser Glu Val Asp Val Asn Thr Ile Leu Val Leu
1               5                   10                  15

Phe Leu His Leu Asp
                20

(2) INFORMATION FOR SEQ ID NO:7:

(i) SEQUENCE CHARACTERISTICS:
        (A) LENGTH: 65 base pairs
        (B) TYPE: nucleic acid
        (C) STRANDEDNESS: unknown (D) TOPOLOGY: unknown (i i) MOLECULE TYPE: DNA (genomic)

(x i) SEQUENCE DESCRIPTION: SEQ ID NO:7:

CTATAAATGT GCATTTATCA GAAGTTGATG TAAACACTAT TCTAGTACTG TTCCTTCATC    60

TAGAT    65

(2) INFORMATION FOR SEQ ID NO:8:

(i) SEQUENCE CHARACTERISTICS:
        (A) LENGTH: 50 amino acids
        (B) TYPE: amino acid
        (C) STRANDEDNESS: unknown
        (D) TOPOLOGY: unknown     (i i) MOLECULE TYPE: peptide     (x i) SEQUENCE DESCRIPTION: SEQ ID NO:8:

```
Gly Pro His Gly Gln Ser Ile Met Leu Gly Leu Asn Ser Val Phe Tyr
 1               5                  10                  15

Pro Ser Ala Ile Ile Arg Gln Ala Ala Pro Phe Phe Asp Phe Cys Trp
            20                  25                  30

Xaa Xaa Xaa Xaa Xaa Xaa Xaa Xaa Xaa Xaa Tyr Lys Cys Ala Phe Ile
            35                  40                  45

Arg Ser
 50
```

(2) INFORMATION FOR SEQ ID NO:9:

(i) SEQUENCE CHARACTERISTICS:
        (A) LENGTH: 63 amino acids
        (B) TYPE: amino acid
        (C) STRANDEDNESS: unknown
        (D) TOPOLOGY: unknown     (i i) MOLECULE TYPE: peptide     (x i) SEQUENCE DESCRIPTION: SEQ ID NO:9:

```
Gly Pro His Gly Gln Ser Ile Met Leu Gly Leu Asn Ser Val Phe Tyr
 1               5                  10                  15

Pro Ser Ala Ile Ile Arg Gln Ala Ala Pro Phe Phe Asp Phe Cys Trp
            20                  25                  30

Xaa Xaa Xaa Xaa Xaa Xaa Xaa Xaa Xaa Xaa Ile Asn Val His Leu Ser
            35                  40                  45

Glu Val Asp Val Asn Thr Ile Leu Val Leu Phe Leu His Leu Asp
 50                  55                  60
```

METHOD OF TREATING THE SYMPTOMS OF ALZHEIMER'S DISEASE

This application is a continuation-in-part of U.S. Ser. No. 803,844 filed Dec. 4, 1991, pending, which in turn is a continuation in-part of U.S. Ser. No. 07/728,267 filed Jul. 11, 1991, now abandoned which is a continuation of U.S. Ser. No. 07/228,364 filed Aug. 4, 1988, now U.S. Pat. No. 5,055,296.

BACKGROUND OF THE INVENTION

1. Field of the Invention

The present invention is directed to a method of treating presenile or senile dementia and to the discovery that a mammalian liver extract that is efficacious in treating such diseases. The present invention is also directed to a method of treating such diseases with this same mammalian liver extract and/or with polypeptides shown in Sequence identification numbers 1-9.

2. Description of the Prior Art

Presenile or senile dementias include Alzheimer's disease, cerebrovascular amyloidosis, dementia associated with Down's Syndrome and Familial Icelandic cerebrovascular amyloidosis.

Alzheimer's disease is the most common form of dementia. About 70% of all cases of dementia are due to Alzheimer's disease. Alzheimer's disease is characterized by memory loss associated with neuronal degeneration in the hippocampus, generation of amyloid plaques in many areas of grey matter, death of neurons with formation of abnormal cytoskeletal structures, and profound cholinergic deficiency. Goldman et al., *Aging of the Brain: Dementia of the Alzheimer's Type* chapter 62, Part x. Development, Critical Periods, and the Emergence of Behavior, 976, 982 (1991). Symptoms of Alzheimer's Disease include a gradual memory loss, decline in ability to perform routine tasks, impairment of judgment, disorientation, personality change, difficulty in learning, and loss of language skills. A progressive, degenerative disease, it eventually renders victims totally incapable of caring for themselves. More than three million Americans are afflicted with Alzheimer's Disease—one in six over the age of sixty-five. After heart disease, cancer, and stroke, it is the fourth leading cause of death in adults.

Mammalian liver extract has been used for the treatment of a wide range of infectious and noninfectious dermatologic conditions, including acne vulgaris, *Journal Invest Dermatology*, 2:205-218 (1939); first and second degree burns, Mississippi Valley *Medical Journey*, 76:199 (1954); sunburn, Clinical *Medicine*, 3:245 (1956); poison ivy dermatitis, *Clin. Med.*, 3:425 (1956) and Herpes zoster, *Southern Medical Journal*, 50:1524 (1957). The active principle and mechanism have not been described. Although some medical practitioners have used liver extract for the treatment of dermatologic conditions, it is not regarded as an antiviral or immune modulator agent even for skin therapy.

Mammalian liver extract has been reported to have bradykinin potentiating activity. Tewksbury et al., *Arch. Biochem. Biophys. (U.S.).* 112, 453 (1965); Tewksbury, *Archives Int'l. de Pharmacodynamie et de Therapie*, 173, 426 (1968); Tewksbury, *Dissertation Abstracts International-Part II*, Vol. 25/04, p. 2214 (1964). Further, one commercially-available liver extract (sold under the trademark KUTAPRESSIN by Kremers-Urban Co., Milwaukee, Wis.) exerts its action, according to product literature, only with respect to tissues that have been injured and when inflammation and edema are present.

In related patent 5,055,296, the use of a heat stable acetone-insoluble, water-soluble mammalian liver extract was shown to be effective in the treatment of mammals infected with nondermatologic viruses, in particular, in the treatment of chronic fatigue syndrome. It has been observed that the clinical symptomatology of chronic fatigue syndrome sometimes resembles a mild form of nonprogressive acquired Alzheimer-like disease. Thus, with this background, the inventors endeavored to discover a method to treat presenile or senile dementia diseases.

SUMMARY OF THE INVENTION

The present invention provides a method of treating presenile or senile dementia disease involving administering to a mammal having said disease a therapeutically-effective amount of mammalian liver extract, the extract being characterized by being heat stable, insoluble in acetone and soluble in water. The terminology "heat stable" means that the liver extract does not lose appreciable activity at temperatures at about 100° C. in water over ten minutes. Additionally, this invention relates to a method of treating presenile or senile dementia disease involving administering to a mammal having said disease a therapeutically effective amount of a peptide or peptide fragment selected from the group consisting of Sequence Identification Nos. 1-9.

BRIEF DESCRIPTION OF THE DRAWINGS

FIGS. 1A and B shows codon bias for His using all pig sequences in GENBANK 66.

DETAILED DESCRIPTION OF THE PRESENTLY PERFERRED EMBODIMENTS

The portion of mammalian liver extract that has been discovered to be effective in treating presenile or senile dementia is the fraction which is heat stable, insoluble in acetone and soluble in water. The liver extract prepared according to the disclosure herein is free from fatty acids, and vitamins, and specifically is free from vitamin B-12, a vitamin naturally occurring in liver. Work in progress suggests polysaccharides may be present in KUTAPRESSIN (Kremers-Urban Co.) in the form of proteoglycans and/or glycoproteins. The same liver extract has been used heretofore in treating skin conditions.

Preparation of the Liver Extract

The liver extract employed in the present invention is prepared by separating a fraction from mammalian livers, preferably porcine liver. The starting material may be a liver preparation as described in *Pharmacopeia of the United States*, Vol. 15, p. 379 (which describes a boiled liver extract suitable for parenteral use), in National Formulary. Vol. XII, p. 222 (which describes an aqueous solution of the thermostable fraction of mammalian liver) or in *National Formulary*, Vol. XI, p. 192-94 (which describes several thermostable liver preparations). Alternatively, the starting material may be fresh liver, frozen liver or a commercially-available liver preparation.

An acetone-insoluble fraction is separated from the starting material. This may be accomplished by admixing a large excess of acetone with the starting material which results in an acetone-insoluble fraction that is separated from the acetone. The treatment with acetone may be repeated. The acetone-insoluble fraction, after being separated from the acetone, is dissolved in water. Any remaining acetone is removed by, for example, distillation. The material effective in treating presenile or senile dementia is contained in the water solution.

Alternatively, and preferably, before the acetone extraction, the starting material is dissolved in water with phenol. The solution is incubated at room temperature and after incubation, the solution is clarified by filtration, and the solution is passed over a cation exchange resin. The resulting resin-treated solution is then concentrated by evaporation, diluted with water, and centrifuged. The acetone-insoluble fraction is then separated from the supernatant by adding a large excess of acetone and further processed as described above.

The acetone-insoluble fraction may be further purified to remove the color pigments by treatment with activated charcoal. For example, the acetone-insoluble fraction may be dissolved in water and contacted with ammonia-activated charcoal.

A pharmaceutically-acceptable preservative usually is added to the water solution. For instance, phenol at from about 0.05 to about 1%, preferably about 0.5% may be added.

The liver extract useful in the present invention may be prepared according to the following examples.

Example 1 Preparation of Liver Extract

Liver Fraction I, described in National Formulary XI, page 193, was dissolved in water to a concentration of 16% by weight. Phenol was added to a final concentration of 1%. The solution was mixed and incubated for seven days at room temperature. It was then clarified by filtration, and diluted to 8% solids by weight in water.

This aqueous solution was then passed three times through a cation exchange resin (sulfonated polystyrene). The resin-treated solution was clarified by filtration and concentrated to 40% total solids by weight by evaporation under vacuum at 65°-70° C. Cold water (5°-10° C.) was added (five volumes of water to seven volumes of liver solution) with mixing. The resultant solution was then centrifuged and the supernatant collected (Sharples-type centrifuge at 1 liter per minute). Phenol was added to a final concentration 0.5-1%.

The solution was adjusted to pH 6.0-7.0, with HCl or NaOH as necessary, clarified by filtration, and heated to 40° C. Then acetone was added (20-30 liters acetone per liter liver solution). The acetone-precipitable material was allowed to settle and most of the acetone was decanted off. The remaining suspension was incubated overnight at room temperature, after which the suspension was diluted to 10 liters with water, and the acetone was removed by distillation. Phenol and water were then added to give a final preparation containing 0.5% phenol and greater than 25 mg total solids per ml (herein designated "KU 10,000").

KU 10,000 was adjusted to pH 6.0-7.0 with HCl or NaOH, as necessary and diluted to 25 mg total solids per ml. with water (i.e., 2.5% by weight solids). The solution was then sterile filtered in suitable vials for use. This final solution is referred to herein as "KU 10,001".

Example II—Physically Active Polypeptide Separation

A large excess of acetone "1800 ml" was added to eight vials KU 10,001 prepared according to Example I, 20 ml/vial, total of 160 ml, and left to stand at room temperature for four hours. After the precipitate settle down at the bottom of the beaker, the clear acetone layer decanted and the remaining suspension centrifuged for five minutes at 3000 RPM. The pellet then dissolved in 160 ml of water and freeze dried to produce about 4.0 g of dry powder consists of 0.3 mg protein/1 mg of dry powder weight. These samples were designated KU 10,172, KU 10,185, KU 10,211, KU 10,244 and KU 10,275

One gram of the dry powder was taken in 7 ml of 50 mM phosphate buffer, pH 7.5 and passed through a 100×2.5 cm column packed with Sephadex G50 suitable for use as a molecular sieve that exclude (does not retard) molecules with a molecular weight greater than 30,000 or BIOGEL p10 which exclude molecules with a molecular weight greater than 20,000. The column was equilibrated with 50 mM phosphate buffer before use at flow rate of 36 ml/hr. The column was eluted with 50mM phosphate buffer pH 7.5. Seven ml. fractions were collected, and read at A280. Fractions were tested for angeotensin converting enzyme inhibition (using Furylacryloylphenylalanylglycylglycine as substrate) as described by Bush, Henry and Slasarchyk; *J. of Antibiotics* 37(4), 330 (1984). All fractions eluted before angeotensin converting enzyme inhibition were pooled according to the following table.

| Loaded KU # | KU # | Pool # | Tube # |
| --- | --- | --- | --- |
| 10,244 | 10,245 | 1 | 22–30 |
|  | 10,246 | 2 | 31–50 |
| 10,185 | 10,190 | 1 | 14–16 |
|  | 10,191 | 2 | 18–20 |
|  | 10,192 | 3 | 21–23 |
|  | 10,193 | 4 | 26–29 |
| 10,275 | 10,275-I | 1 | 35–46 |
|  | 10,275-II | 2 | 47–58 |
|  | 10,275-III | 3 | 59–68 |

All pooled samples were concentrated, dialyzed in cellulose dialysis tubing with a molecular weight cut off of 1,000 and lyophilized.

Example III—Physically Active Polypeptide Separation

KU 10,172 prepared according to Example II was fractionated on reverse phase $C_{18}$ prep column, eluted with buffer A: 20mM ammonium acetate pH 7.0, B: 80% acetonitrite in buffer A, gradient run at 214 nm, programmed: zero to 80% B in 80 min. at 8.4 ml/min. Fractions collected 8.4 ml/test tube. All tubes were analyzed by analytical $C_{18}$ reverse phase column and size exclusion high pressure liquid chromatography column Tsk 125 and pooled to twelve fractions based on its retention times. Eight fractions KU 10,201 to KU 10,208 were tested for anti-viral activity and showed a significant cell protection activity.

Example IV—Further Purification of Physically Active Polypeptide

KU 10,203 and KU 10,207 prepared according to Example III were further purified on reverse phase $C_{18}$ prep column, eluted with buffer A: 20 mM ammonium actuate pH 7.0, B: 80% acentonitrite in buffer A, gradient run at 214 nm, programmed: Zero to 80% B in 80 min, at 8.4 ml/min. Fractions collected 8.4 ml test tube. All tubes were analyzed by analytical $C_{18}$ reverse phase column and size exclusion high pressure liquid chromatography column (Tsk 125) and pooled according to its retention times to produce KU 10,214 and KU,215. The cDNA from rat liver for the KU 10,214 and KU 10,215 fractions that were active in the bioassay was isolated and cloned using the polymerase chain reaction technique. The desired sequence to be amplified was that of the gene in pig liver cells that encodes the peptides in the KU 10,214 and KU 10,215 fractions.

Active Fraction Peptide Amino Terminal Amino Acid Sequencing

Ten amino acids of amino terminal sequence of KU 10,214 and KU 10,215 were determined by Edman degradation using an Applied Biosystems model 477A automated peptide sequencer with attached High Pressure Liquid Chromatography model 120A on-line phenyl isothiocyanate analyzer found to be (Ala or Val or Ile) Glu (His or Pro) Gly (Tyr or Met or Thr) His Gly Pro His Gly. More specificially, KU 10,214 has the amino acid sequence:
(Ala or Val or Ile) - (Glu or Gln) - (His or Pro or Arg) - Gly - Thr - His - X - pro - His - Gly
KU 10,215 has the amino acid sequence:
(Ala or val or ILe) - (Glu or Gln) - (His or pro) - Gly - (Tyr or Met) - His - Gly - X - His - Gly - X - X - Gly -X- Gln Due to the similarity of both sequences, we proposed a sequence to be used for our Polymerase Chain Reaction (PCR) work using the following deca peptide sequence.
Ala - Glu - His - Gly - Tyr - His - Gly - Pro - His - Gly.

Polymerase Chain Reaction Primer Design

Figures 1A, 1B:
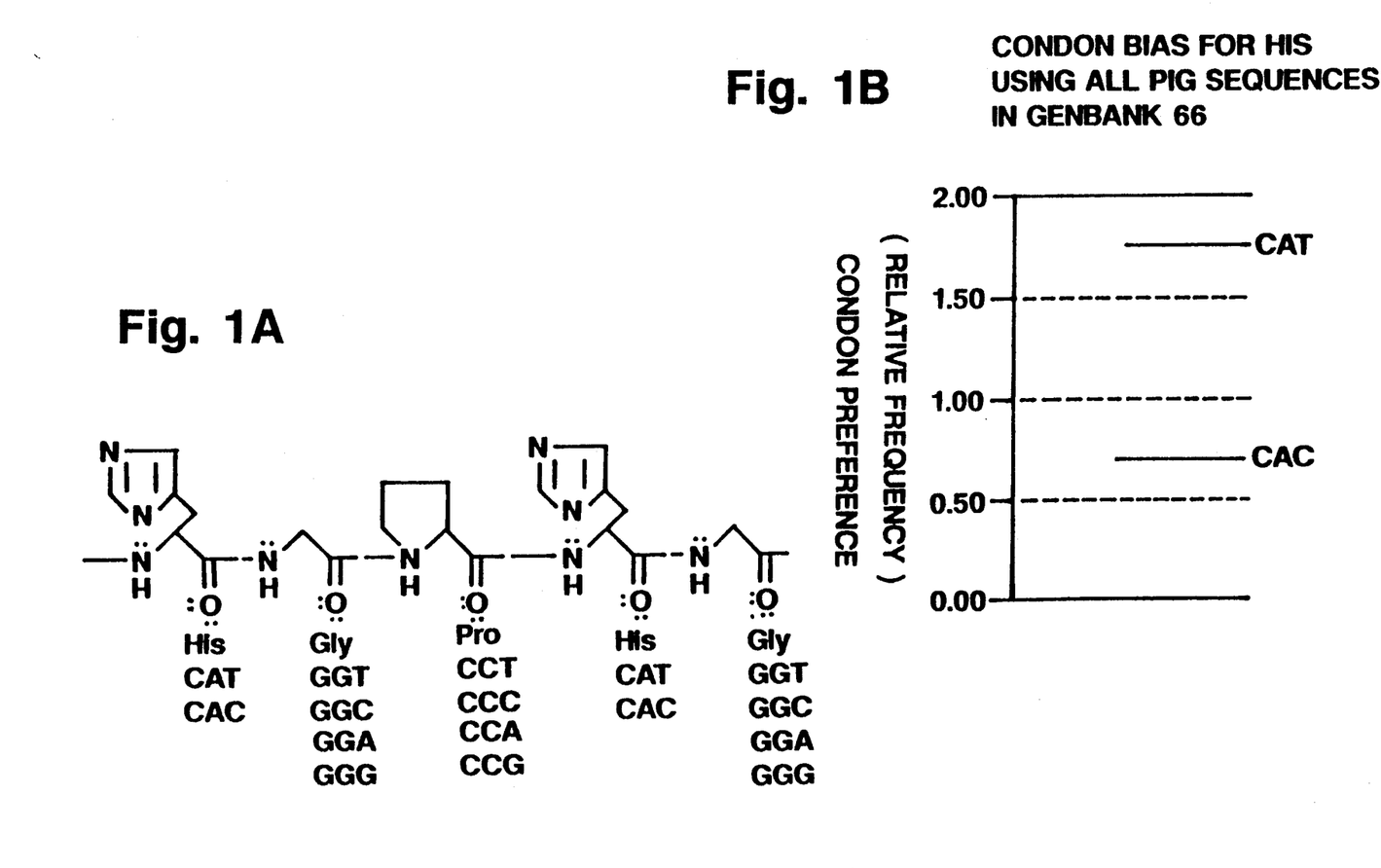

The oligonucleotide primer 5'CATGGICCICATG-GI3' [I indicates Inosine] was designed based on the five amino acid sequence (HGPHG) region sequence that was common to both the KU 10,214 and KU 10,215 fractions active in the bioassay. This primer corresponds to the indicated amino acids regardless of codon usage except for His. Codon bias analysis for all pig gene sequences found in the databank Genbank 66 showed His codon at CAT to be used about 2.5 time as often as His codon CAC. This and the rarity of CG dinucleotides in peptide coding regions of mammalian genomes (Sambrook, J., Fritsch, E. F. and Maniatis, T. (1989) in "Molecular Cloning: A Laboratory Manual", 2nd edition, Cold Spring Harbor Laboratory, Cold Spring Harbor, New York) dictated use of CAT and not CAC for His in this sequence producing a primer sequence of 5'CATGGICCICATGGI 3'. This primer was prepared by conventional techniques using an Applied Biosystems DNA synthesizer. See FIGS. 1A and B.

RNA Isolation

Total RNA (2.5 mg) was isolated from 1.5 grams of fresh liver tissue from a female pig by rapid homogenation in guanidine thiocyanate followed by extraction with phenol (Chomczynski, P. and Sacchi, N. (1987) Anal. Biochem 162, 156-159). After two successive precipitations with isopropanol, the purified RNA was dissolved in water. The RNA was then subjected to poly(U) Sepharose chromatography, (Jacobson, A. (1987) Meth. Enzymology 152, 254–261), which yielded 21 μg of Poly(A)+RNA from 1 mg of total RNA.

cDNA Synthesis and Intermediate Polymerase Chain Reaction Amplification

Double stranded cDNA was prepared from the Poly-(A)+RNA by a modification of the method of Gubler and Hoffman (Gene 25, 283 (1983)). Five μg of Poly-(A)+RNA was used with an oligo(dT)-Hind III primer and AMV reverse transcriptase to synthesize the first strand, and second strand conversion was accomplished using RNase H and E. Coli DNA polymerase I. The yield was 30% first strand conversion and 100% second strand conversion. The double stranded cDNA was extracted with phenol and precipitated with ethanol by conventional methods. After treatment with T4 DNA polymerase to flush the ends, the cDNA was ligated with UNIAMP adaptors (Clontech Labs Inc. 800-662-CLON) under conditions described by the manufacturer. Following ligation, 3μl of a 1:10 dilution of the cDNA was amplified by polymerase chain reaction in the Perkin Elmer Cetus GENEAMP System using a single UNIAMP primer (Clontech) under conditions described by the manufacturer. A sample of the reaction products was analyzed by agarose gel electrophoresis in the presence of ethidium bromide. The results showed a distribution of cDNA products that closely matched the pattern of unamplified cDNA. The remainder of the reaction products were purified by extraction with phenol and SEPHAROSE (Pharmacia Co.) CL-4B chromatography. These intermediate amplification and purification steps produced a sufficient amount of pure cDNA free of extraneous sequences which could have interfered with subsequent procedures.

Polymerase Chain Reaction Amplification with the Specific primer

Figure 2A:
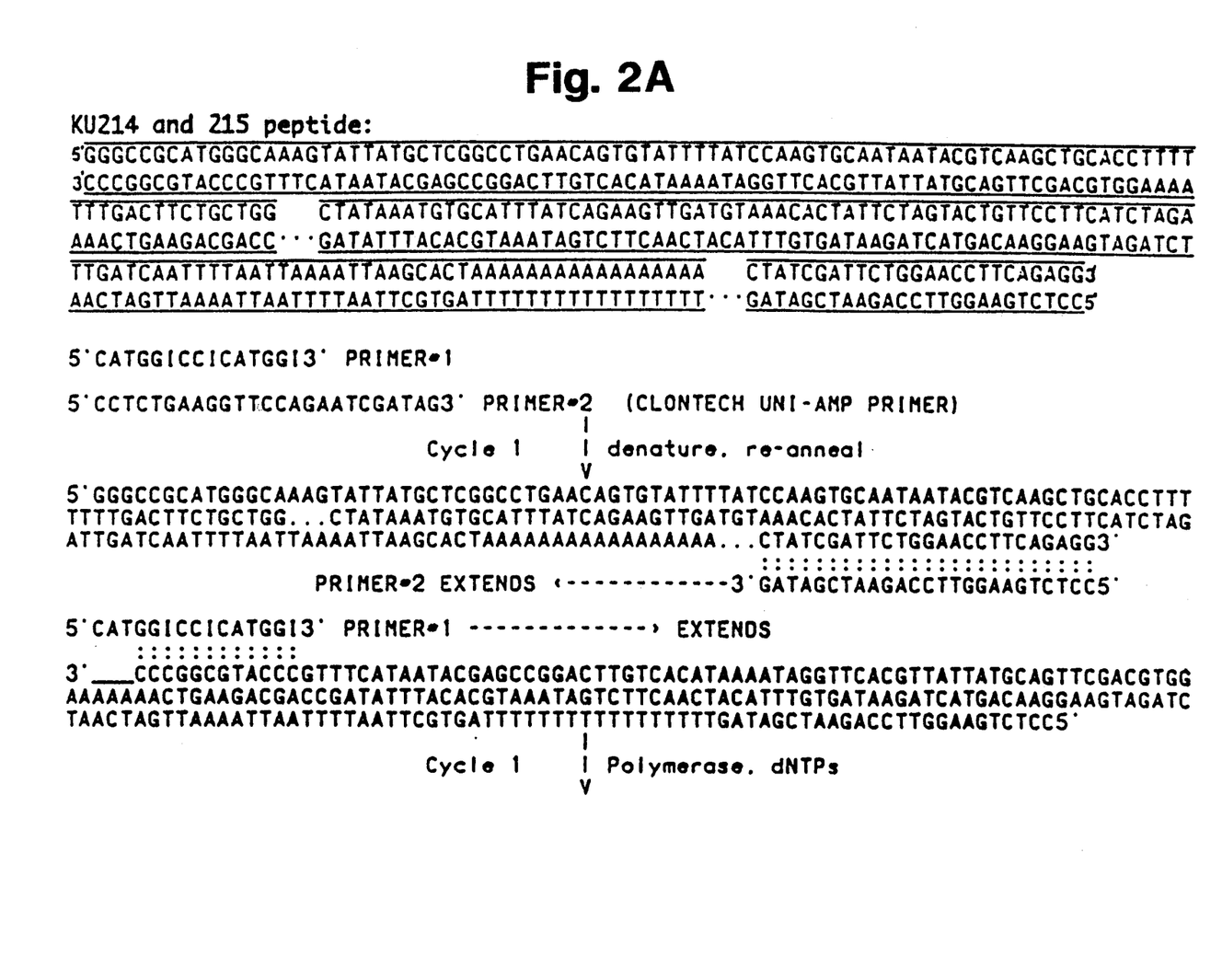
FIGS. 2A and B illustrates the strategy used for sequencing the active peptide.
Figure 2B:
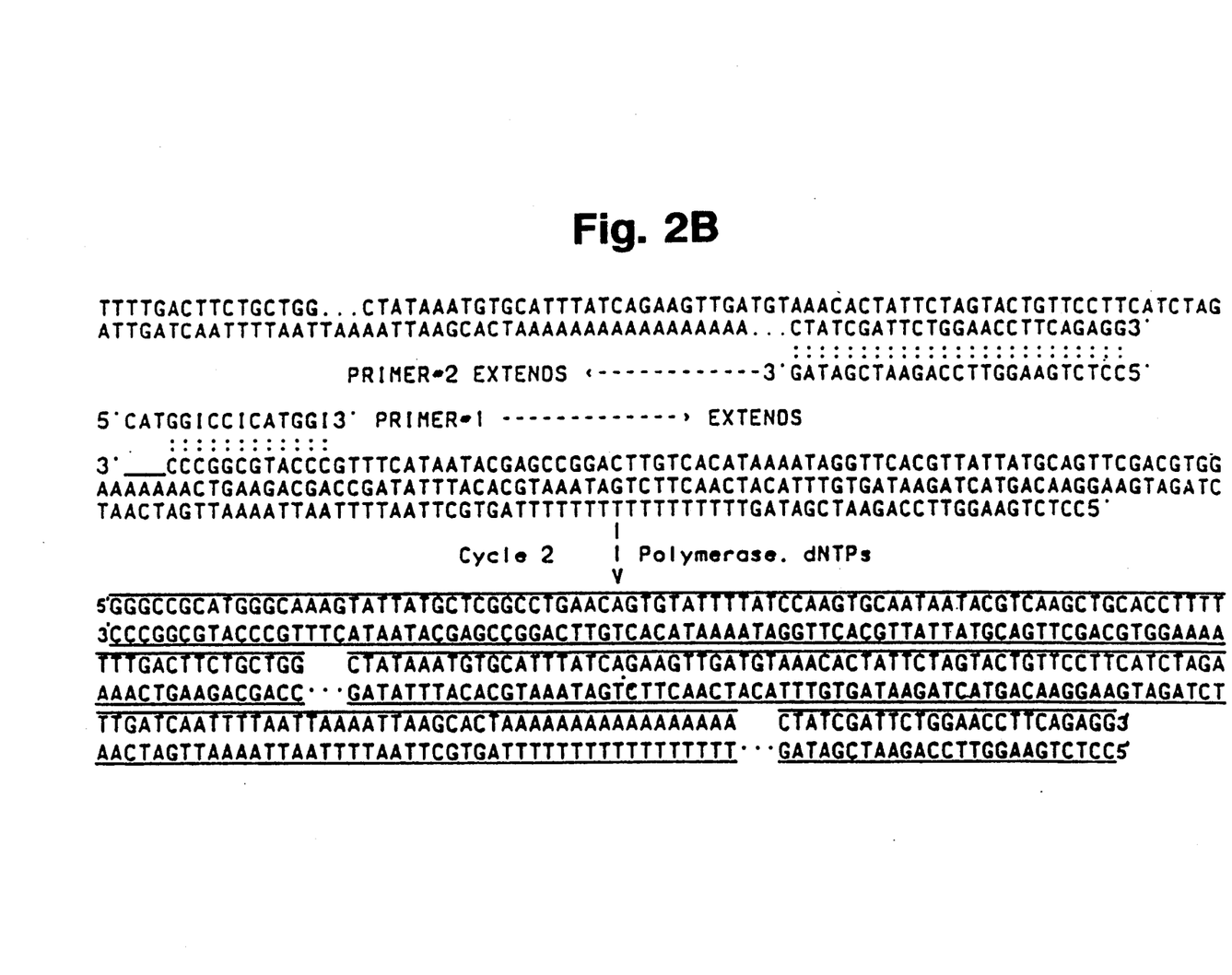

The amplified cDNA was precipitated with ethanol, collected by centrifugation and dissolved in 20 μl water. A 1 μl sample was used for polymerase chain reaction amplification with the specific primer described above in combination with oligo (dT)-Hind III primer. Conditions for polymerase chain reaction were 30 cycles at 94° C. for 1 minute, and 72° C. for 2 minutes per cycle, with a final extension at 72° C. for 5 minutes. A fraction of the reaction products were analyzed by agarose gel electrophoresis in the presence of ethidium bromide. The results showed 3 major DNA species in the range of 200 bp (base pairs), 400 bp and 500 bp. Control reactions in which the primers were omitted produced no detectable products. The strategy for sequencing this DNA is shown in FIGS. 2A and B.

Cloning of the Polymerase Chain Reaction products

The remainder of the polymerase chain reaction products was treated with T4 DNA polymerase to flush the ends, and then purified by phenol extraction and ethanol precipitation. The DNA was ligated with ECOR I linkers under standard conditions. Following digestion with ECO RI and Hind III and removal of small molecules by SEPHAROSE (Pharmacia Co.) CL-4B chromatography, the prepared DNA was ligated with ECO RI/Hind III EXLOX vector arms, packaged in vitro, and plated on E. Coli by standard methods. The resulting library contained $3 \times 10^5$ independent clones and was amplified to a titer of $3 \times 10^{10}$ pf μ/ml.

Verification of cloning

The library was plated at a density corresponding to approximately 1,000 plaques per 82 mm plate. Plaque lifts were prepared and hybridized with random-primer labeled DNA probes by conventional methods. Using a probe from DNA amplified with the specific primer described above, virtually every plaque produced a positive hybridization signal. This indicated the library contained the desired inserts of polymerase chain reaction products.

DNA sequencing

Six randomly chosen plaques were converted to plasmid subclones for DNA sequence analysis. Restriction enzyme analysis showed an insert of approximately 500 bp in four of these isolates. Plasmid DNA was prepared and sequenced directly using T7 DNA polymerase (promega) and chain-terminating dideoxynucleotides (Mierendorf, R. C. and Pfeffer, D. (1987) Meth. Enzymol. 152, 556-562).

DNA Sequencing

Sequencing experiments determined 96 base pairs at the 5' end and 110 pairs at the 3' of the cDNA insert, which appeared to be identical in the clones sequenced.

The 5' 96 base pairs encoded a 32 amino acid polypeptide (Sequence Id. No. 1) whose first four amino acids GPHG corresponded to those of the primer HPGHG. (Sequence Id. No. 2) The 110 pairs at the 3' end (Sequence Id. No. 3) had a TAA or ATG stop codon in all three reading frames, so the C-terminal of the polypeptide is L (encoded by 5'CTA3'), (Sequence Id. No. 4 which has 8 amino acids and is encoded by (Sequence Id. No. 5) and/or (Sequence Id. No. 6) which has 21 amino acids and is encoded by Sequence Id. No. 7. As such the polypeptides are characterized by the Sequence Id. No. 1 at the 5' end and Sequence Id. Nos. 4 and 6.

Example V Physical and Chemical Tests on Physiologically Active Polypeptide

Thus, the physiologically-active polypeptide may be characterized by its physical and chemical properties. The active polypeptide is insoluble in acetone, and soluble in water. It has a molecular weight as determined by molecular sieve chromatography experiments to be about 5,000–40,000.

In animals, Scrapie is a transmissible animal model of Alzheimer's disease. Prusiner et al., Prion diseases of the Central Nervous System, Monographs Path. 32:86-122 (1990). Scrapie is caused by a prion. A prion is a transmissible pathogen that causes degenerative diseases in humans and animals. Prions are composed largely, of an abnormal isoform of the prion protein (PrP). Prion proteins relating to Scrapie have been identified and are listed in the protein identification resource computer data base from National Biomedical Research Foundation. A search of this data base revealed that KU 10,215 polypeptide has certain sequence homology with both normal and abnormal isoforms of the prion that in its abnormal isoform causes Scrapie. As such it was theorized that KUTAPRESSIN (Kremers-Urban Co.) could be administered to a mammal to potentially treat presenile or senile dementia.

ADMINISTRATION OF POLYPEPTIDES

The polypeptides useful in the present invention preferably are administered by injection, for example, intramuscular injection. However, other forms of administration are contemplated. The polypeptides may be employed in the form of pharmaceutically-acceptable salts of the components, such as the alkali metal salts. The pharmaceutically-acceptable amides, lower alkyl esters, protected derivatives, other derivatives and analogues of the components of the polypeptides are also contemplated.

Although, as indicated, the polypeptides may be used as a water solution, it may also be utilized in association with other pharmaceutical carriers, for example, in saline solution. In any case, since the polypeptide is preferably administered by injection, it is contemplated that the extract will be contained in a water base carrier. A preferred product is a polypeptide water solution containing about 2.5% by weight of polypeptide. More generally, the polypeptide ranges from 5 µg to 500µg per ml of carrier.

ADMINISTRATION OF LIVER EXTRACT

The acetone-insoluble liver extract useful in the present invention preferably is administered by injection, for example, intramuscular injection. However, other forms of administration are contemplated.

The liver extract may be employed in the form of pharmaceutically-acceptable salts of the components, such as the alkali metal salts. The pharmaceutically-acceptable amides, lower alkyl esters, protected derivatives, other derivatives and analogues of the components of the liver extract are also contemplated.

Although, as indicated, the liver extract may be used as a water solution, it may also be utilized in association with other pharmaceutical carriers, or example, in saline solution. In any case, since the liver extract is preferably administered by injection, it is contemplated that the extract will be contained in a water base carrier. A preferred product is a water solution containing about 2.5% by weight of liver extract solids.

Dosages may vary depending upon the condition of the patient. Generally, however, it has been found that the administration of 2 ml. of KU 10,001 prepared as described in Example 1 intramuscularly every other day will produce beneficial results in as little as about 4 weeks.

TEST RESULTS

A number of Alzheimer's patients were treated with KUTAPRESSIN (Kremers-Urban Co.). To quantify the patients conditions they were assessed on the global deterioration scale (GDS). The GDS is a 7 point rating system for the staging the magnitude of cognitive and functional capacity in normal aging, age-associated memory impairment, and primary degenerative dementia of the Alzheimer type. Seven GDS stages include:

Stage 1: normal, neither subjective nor objective evidence of cognitive deficit.

Stage 2: very mild cognitive decline, with subjective evidence only of cognitive decline—considered normal for age.

Stage 3: mild cognitive decline in which objective evidence of decline is manifest but subtle—the patient may have incipient or questionable dementia, age-associated memory impairment, or other problems.

Stage 4: moderate cognitive decline of sufficient magnitude to meet accepted criteria for mild dementia—deficits are readily seen in the clinical interview and affect complex activities of daily living.

Stage 5: moderately severe cognitive decline corresponding to a moderate severity of dementia—the deficits seen are sufficient to interfere with independent survival and functioning.

Stage 6: severe cognitive decline corresponding to moderately severe dementia—deficits interfere with basic activities of daily living.

Stage 7: very severe cognitive decline corresponding to severe dementia—deficits interfere with all activities of daily living.

M. Davidson, The Psychiatric Clinics of North America Alzheimer's Disease. 14(2) :316 (1991 W. B. Saunders Co.)

Patient A

This 71 year old white male retired electrician was evaluated on Dec. 3, 1991 for response to KUTAPRESSIN (Kremers-Urban Co.) treatment. His history is as follows: He was born in Lyndale, Texas and is of German descent. He completed two years of junior college and was offered a scholarship to Rice University but was unable to attend due to a head injury. He was hit in the head with a baseball and this was followed by garbled speech and seizure disorder. His last seizure was in 1945, but he was continued on phenobarbital until 1983.

The present illness began in 1987 when his wife first noted he was becoming slightly forgetful. He became disoriented as to his location while driving in a previously familiar area of Houston. His wife describes him as becoming slowly more forgetful and "willful" from 1987 to 1991. In June of 1990, he told his daughter he saw ants on the deck although no ants were observed and saw people in the trees that were not there. In February of 1990 his Doctor told him to stop driving because he had become forgetful and had poor coordination. In December of 1990 he traveled to Kentucky with his wife who noted he became disoriented in the airport. His wife became ill in January of 1991 and was hospitalized three days, returned home to find Patient A hallucinating and paranoid. He was then evaluated by a neurologist but did poorly over the next several months with severe nocturnal restlessness. He would walk around the house at night with a flashlight hallucinating—thinking he saw people in the house. He was treated with Haldol but became argumentative, hallucinated that he saw "fire in the street", and became violent and unmanageable.

He was then hospitalized for one month. He spent 48 hours in restraints when first admitted. His wife reported that he was given extensive tests and Alzheimer's disease was diagnosed with discharge to a nursing home suggested. His wife instead took him home on May 23, 1991 and describes him at that time as "like a zombie". He was discharged on Prolixin 25 mg h.s. and Calan ½ cap qd for high blood pressure (on for last 2 years). His Prolixin was decreased Jun. 23, 1991 to 5 mg h.s. His wife reported he had little interest in his surroundings and was confused and disoriented. He developed persistent diarrhea Jul. 1, 1991 and was begun on KUTAPRESSIN (Kremers-Urban Co.) 2 cc IM gd on Jul. 26, 1991. KUTAPRESSIN (Kremers-Urban Co.) was decreased to 2 cc IM 5 days per week on Sep. 26, 1991 and decreased to three days per week on Oct. 24, 1991.

After four weeks on KUTAPRESSIN (Kremers-Urban Co.) the following improvements were noted by patient's wife and others:

1) Patient A was able to tie his own tie. Patient had been able to do this previously.
2) Patient A's shuffling gait has improved—now has "spring to his step" per wife. Wife reported that he could only shuffle along, but now he is able to do a "brisk walk."
3) Patient A no longer falls over when car goes around a corner. Before KUTAPRESSIN (Kremers-Urban Co.) this would occur and he could not right himself without assistance.
4) Patient A could not shower without being told step-by-step what to do; he now showers unassisted.
5) Patient A could not dress himself before KUTAPRESSIN (Kremers-Urban Co.) treatment; he now dresses himself.
6) Patient A could not follow TV and would not watch it; now watches TV, especially baseball and football, with interest.
7) Patient A would not read newspaper (could not follow); now reads newspaper.
8) Patient A reports that he remembers that he was unable to tie his shoes and now can tie them.
9) Patient A could walk less than ½ block; he now walks four to six blocks outdoors and walks in grocery store and mall without difficulty. He had "no strength" but now is stronger and can carry wood.
10) Patient A was unable to write checks before, due to confusion, but after two months on KUTAPRESSIN (Kremers-Urban Co.) regained his ability to write checks. For example he wrote two checks to his church last month.
11) Patient A reports that before treatment he became lost at church when he went to the restroom; he could not find his way back. Now has no problems like this and returns without difficulty from restroom at church.
12) Before treatment Patient A could not sign his name unless it was spelled out to him a letter at a time. Now he signs name on his own without difficulty.
13) Before treatment Patient A was confused and thought deceased relatives were still alive. Example: would call his aunt Aija by name although she died in 1979. This has all resolved on treatment and he, during the interview, correctly recalled parents and aunt Aija as being deceased.
14) Patient A had no problems feeding himself or with bowel or bladder control before treatment, but was unable to make choices between foods offered by his wife. He is now able to make choices.

Present clinical impression: Patient A was initially assessed as stage 6 GDS and is now stage 4.
Alzheimer's disease is in partial remission while receiving KUTAPRESSIN (Kremers-Urban Co.).

Patient B

This 83 year old white female retired secretary is being evaluated for possible response to KUTAPRESSIN (Kremers-Urban Co.) treatment. The history is obtained from the patient's daughter with occasional nods of agreement for the patient but no real specific information from patient. The patient interrupted the interview several times in a polite way to say "This all began about a week ago."

Present illness was first noted about 1984 when she became forgetful, misfiled papers in her job as a church secretary, and began placing bookkeeping figure in wrong columns. She has slowly deteriorated since. She saw a doctor in 1990 for evening flights of fancy and disorientation and Alzheimer's was diagnosed. She saw a neurologist November of 1990 who did extensive tests including EEG and confirmed Alzheimer's disease. In the last four months of 1990 she began exhibiting nocturnal enuresis about three times per week.

In early 1991 she was very forgetful, incoherent "regressed", and could barely get out of bed. Hydergine Rx was tried in the spring of 1991 but this treatment made her "mean" with no real improvement, and it was discontinued. She was diagnosed as a stage 7 GDS. She was begun on KUTAPRESSIN (Kremers-Urban Co.) 2 cc IM qd.

By Mar. 11, 1991 the patient was improved mentally but her husband died unexpectedly on that day of an MI. She was then moved in with her daughter. The KUTAPRESSIN (Kremers-Urban Co.) frequency was decreased in April of 1991 after six weeks of treatment to three times a week, and since 7/91 she has been on 2 cc IM once per week.

Since being on KUTAPRESSIN (Kremers-Urban Co.) her daughter has noted:
1) Patient B's forgetfulness has stopped worsening:
2) Patient B's nocturnal enuresis has completely disappeared and not recurred.
3) Before treatment Patient B would not watch TV. Now she watches sports and football in the evenings but "can't remember any of it.
4) Patient B has not recovered her ability to sew, a lifelong hobby, and spends much of her time "wandering around the house". Since KUTAPRESSIN (Kremers-Urban Co.) treatment she does seem less apathetic, wants to get out of the house and go for a drive, and has recovered her ability to set the table though occasioally puts on a few extra spoons.
5) Before treatment Patient B couldn't dress herself, could not bathe herself and couldn't put her makeup on. After KUTAPRESSIN (Kremers-Urban Co.) she is able to dress herself (although her daughter picks out her outfits), bathes herself (including drawing her own bath and getting in and out of tub herself), and puts her own makeup on.
6) Patient B reads newspaper now but "can't remember any of it".
7) Overall, daughter thinks progression of patient's Alzheimer's disease has been halted by KUTAPRESSIN (Kremers-Urban Co.) but since dose was decreased July of 1991 some deterioration has been noted such as increased shuffling and stumbling noted six weeks ago. She still loses her way at church. The daughter reports that Patient B has "more stamina, spark, fire, life" since on KUTAPRESSIN (Kremers-Urban Co.).

Current Diagnosis:
1) Alzheimer's Disease, long standing on KUTAPRESSIN (Kremers-Urban Co.), with some improvement:
   A) Resolution of nocturnal enuresis
   B) Recovery of ability to dress herself, bathe herself, and apply her makeup.

The patient is now a stage 5 GDS. M. Davidson, The Psychiatric Clinics of North American Alzheimer's Disease. 14(2):316 (1991 W. B. Saunders Co).

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. A method of treating the symptoms of Alzheimer's disease comprising administering a therapeutically effective amount of a mammalian liver extract which is referred herein as KU 10,001, wherein the extract is heat stable, insoluble in acetone and soluble in water.

2. The method of claim 1 wherein the liver extract is a porcine liver extract.

3. The method of claim 1 wherein the liver extract is in a pharmaceutically-acceptable carrier at a concentration of about 2.5% by weight solids.

4. The method of claim 2 wherein the liver extract is in a pharmaceutically-acceptable carrier at a concentration of about 2.5% by weight solids.

5. The method of claim 4 wherein the liver extract is in water.

* * * * *

UNITED STATES PATENT AND TRADEMARK OFFICE
CERTIFICATE OF CORRECTION

PATENT NO. : 5,284,664
DATED : February 8, 1994
INVENTOR(S) : Wagle et al.

It is certified that error appears in the above-indentified patent and that said Letters Patent is hereby corrected as shown below:

Column 10, line 5, delete "able" and insert -- unable --.

Column 11, line 37, delete "occasioally " and insert -- occasionally --.

Signed and Sealed this

Twenty-sixth Day of July, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,284,664
DATED : February 8, 1994
INVENTOR(S) : Wagle et al.

It is certified that error appears in the above-indentified patent and that said Letters Patent is hereby corrected as shown below:

In drawing 1B delete "CONDON" and insert -- CODON --;
In Column 5, line 22, delete "Gin" and insert -- Gln --;
line 23, delete "pro" and insert -- Pro --;
line 25, delete "val" and insert -- Val --, delete "ILe" and insert -- Ile --, delete "Gin" and insert -- Gln --, delete "pro" and insert -- Pro --;
line 27, delete "Gin" and insert -- Gln --.
In Column 10, after "Patient A was able to tie his own tie. Patient" insert -- was --.

Signed and Sealed this

Twenty-third Day of August, 1994

Attest:

BRUCE LEHMAN

*Attesting Officer*   *Commissioner of Patents and Trademarks*